United States Patent [19]
Krumeich

[11] Patent Number: 6,071,293
[45] Date of Patent: Jun. 6, 2000

[54] AUTOMATIC MICROKERATOME

[76] Inventor: Jörg H. Krumeich, Probst-Hellmich-Promenade 28, 44866 Bochum, Germany

[21] Appl. No.: 09/354,597

[22] Filed: Jul. 16, 1999

Related U.S. Application Data

[63] Continuation-in-part of application No. 09/067,146, Apr. 27, 1998, abandoned.

[30] Foreign Application Priority Data

Apr. 25, 1997 [EP] European Pat. Off. ............ 97 106 949

[51] Int. Cl.$^7$ ..................................................... A61F 9/00
[52] U.S. Cl. ............................................................. 606/166
[58] Field of Search .................................. 606/166, 167, 606/161, 169, 172, 107

[56] References Cited

U.S. PATENT DOCUMENTS

| | | | |
|---|---|---|---|
| 4,796,623 | 1/1989 | Krasner et al. | 606/166 |
| 4,840,175 | 6/1989 | Peyman . | |
| 5,496,339 | 3/1996 | Koepnick . | |
| 5,690,657 | 11/1997 | Koepnick . | |
| 5,989,272 | 11/1999 | Barron et al. | 606/166 |

FOREIGN PATENT DOCUMENTS

| | | |
|---|---|---|
| 0442 156 A1 | 8/1991 | European Pat. Off. . |
| 0771553A1 | 10/1996 | European Pat. Off. . |
| WO 95/31143 | 11/1995 | WIPO . |

*Primary Examiner*—Michael Buiz
*Assistant Examiner*—Kevin Truong
*Attorney, Agent, or Firm*—Clifford A. Poff

[57] ABSTRACT

An apparatus for transverse planar cutting of cornea to expose a corneal surface to allow correction of myopia, apparatus including a corneal suction ring including a cornea engaging surface on side thereof and microkeratome guide surfaces on an opposite site, the guide surfaces being spaced apart, parallel and extend along opposite site of an aperture arranged for exposing a portion of a cornea, a shift member releasably mounted to an outer wall of the suction ring, a microkeratome including a cutting blade driven by a motor to execute a transverse planar cutting of cornea surface exposed by the cornea suction ring, the microkeratome cutting head having guide surfaces, engaging the corresponding guide surfaces on the cornea suction ring, and an actuator connecting the shift member and the microkeratome for controlling relative movement between the corneal suction ring and the cutting head of the microkeratome.

8 Claims, 4 Drawing Sheets

AUTOMATIC MICROKERATOME

CROSS REFERENCE TO RELATED APPLICATION

This application is a Continuation-In-Part of U.S. patent application Ser. No. 09/067,146, filed Apr. 27, 1998 now abandoned.

FIELD OF THE INVENTION

This invention relates to an apparatus for effecting a planar cutting of the cornea to form a lamella cutting attached by a hinge of corneal tissue to allow treatment by a laser for correction of myopia.

DESCRIPTION OF THE PRIOR ART

There has been established since about the beginning of 1990 the use of laser treatment for the correction of myopia. When the condition of myopia requires larger corrections to the corneal shape, the principal of LASIK (LASIK=Laser in situ keratomilausis) is employed. As illustrated in FIG. 1, this method consists of cutting a thin parallel lamella 1 of corneal tissue from the surface of the cornea 2. To aid in the cutting process a distance holder 3 included in the microkeratome aids in the formation of lamella. The corneal lamella remains attached by a hinged portion 4, as shown in FIG. 2, of corneal tissue and thereafter the microkeratome is retracted from the cornea. The flap is then held back and a laser beam 5 is used for treatment of the inside tissue 6 of the cornea. Thereafter as shown in FIG. 3 the flap is repositioned on the cornea. The flap is only 13/100 to 18/100 of a mm thick. A suture is not needed as osmotic forces hold the flap in place. The procedure of forming a lamella corneal flap to expose corneal tissue for laser treatment offers the advantage of faster healing, less discomfort for the patient and more stability.

Multiple microkeratomes have been developed over the years, all following the same principal of primarily creating a flat surface on the cornea, whereafter the cut is performed similar to a carpenter's plane. A motor is used to move the blade in all microkeratome and in some microkeratomes rotates the blade. There is a known microkeratome using one motor for movement of both the blade and the microkeratome.

The movement of the microkeratome to execute the corneal cutting is performed on a suction ring that surround the corneal circumferences and is adhered firmly to the corneal dome. The position of cornea within the suction ring allows the microkeratome to create a flat corneal surface form the corneal dome. The movement of the microkeratome on the ring is guided within guides.

Another type of microkeratome (Koepnick, U.S. Pat. Nos. 5,496,339 and 5,690,657) comprises a corneal suction ring combined with guides for a cutting blade driven by drive mechanism. The apparatus of the suction ring is covered by a transparent insert including a face having a surface portion shaped according to a predetermined correction of the cornea. The cutting blade is guided in a plane immediately adjacent to the under surface of the transparent insert and a parallel to this surface whereby only the cutting edge of the cutting blade traverses the insert. The cutting blade extends in a guide recess in a plane of the suction ring parallel and adjacent to the face of the insert in advance of the superstructure of drive mechanism.

A disadvantage of this know microkeratome is that the suction ring, the cutting blade, the guides and the drive mechanism are parts of a large interconnected structure which is undetachable and difficult to handle by the physician prior to and during operation. It would be desirable to handle at least the suction ring as a separate part so as to adjust the suction ring alone on the cornea in the correct position prior to operation and to attach the microkeratome and its driving mechanism later.

It is an object of the present invention to provide an apparatus as mentioned above having a detachable suction ring without forfeitures with respect to exact guide and precise control of movement of the microkeratome.

It is a further object of the present invention to secure an electronically geared stepping motor to a microkeratome and use a shift member to form a releasably locked interconnection between the output of the stepping motor and a corneal suction ring for controlling cutting of corneal tissue.

SUMMARY OF THE INVENTION

According to the present invention there is provided an apparatus for transverse planar cutting of a cornea to expose a corneal surface to allow correction of myopia, said apparatus including:

a corneal suction ring comprising a cornea engaging surface on one side thereof and microkeratome guide surfaces at the opposite side thereof extending parallel along opposite sides of an aperture in said suction ring for exposing a portion of the cornea;

a microkeratome to execute at least a partial transverse cut of cornea surface when moving across said aperture of said suction ring, said microkeratome comprising a cutting head, a motor housing and a motor for oscillating movement of a cutting blade guided in said cutting head, whereby said cutting head is provided with guide surfaces insertable for mating engagement into the guide surfaces of said suction ring, and an electronically controllable actuator for controlling relative movement between said suction ring and said cutting head comprising an actuator housing and a stepping motor within this housing to drive a shift member which is linear displaceable relatively to this housing, whereby the actuator housing is rigidly connected to combined with the motor housing of said microkeratome and said shift member is releasably connected to said suction ring.

This apparatus enables the physician to apply at first the corneal suction ring on the cornea in its correct position and then to insert the cutting head of the microkeratome into the guide surfaces of the suction ring to achieve an accurate guiding and to couple the shift member of the actuator to the suction ring so as to control precisely the relative movement between said suction ring and said cutting head.

Preferably said shift member extends radially from said suction ring and in a generally parallel central relation to the guide faces of the suction ring.

To simplify the attachment and detachment of the shift member the suction ring includes a receiver having a cavity for receiving an end portion of said shift member and a retainer supported by the suction ring to maintain a releasable interconnected relation between the shift member and the suction ring, whereby said end portion of said shift member is insertable into said receiving cavity in the direction of its displacement.

To improve the guiding characteristics of the mating surfaces the guide surfaces of the suction ring and of the cutting head have dove tail form.

According to an alternative embodiment of the invention said shift member is a flat flexible steel band. This feature makes it possible to arrange the actuator in an optional position relatively to the suctioning, for example parallel to the motor housing of the microkeratome.

Preferably said cutting head is detachably mounted to said motor housing of microkeratome. This feature makes it possible to desinfect the suction ring, the cutting head and the drive mechanisms separatively according to different requirements.

To allow the physician a better view to the field of operation before and during the operation said cutting head comprises an a applanation plate having a transparent window in front of the cutting edge of said cutting blade.

BRIEF DESCRIPTION OF THE DRAWINGS

The present invention will be more fully understood when the following description is read in light of the accompanying drawings in which.

DETAILED DESCRIPTION OF THE PREFERRED EMBODIMENT

Figure 1:
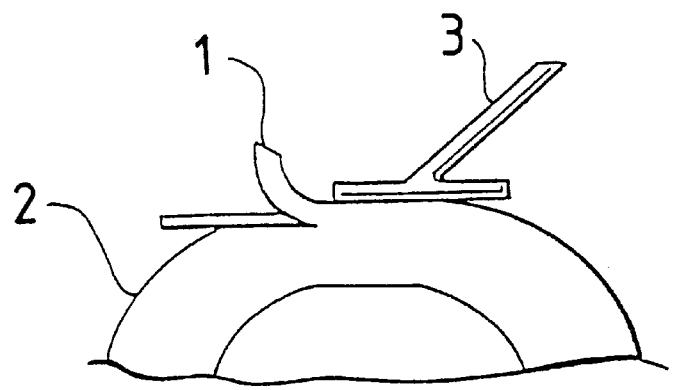
FIG. 1 is a schematic illustration showing the use of a microkeratome for executing a cut of hinged lamella portion of a cornea to allow laser treatment for correction of myopia.
Figure 2:
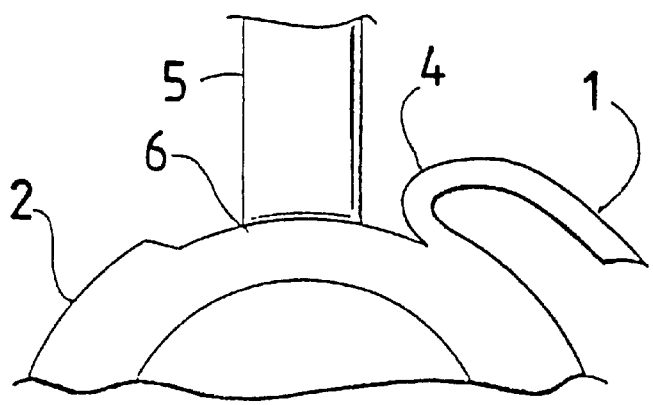
FIG. 2 is a schematic illustration of the laser correction treatment.
Figure 3:
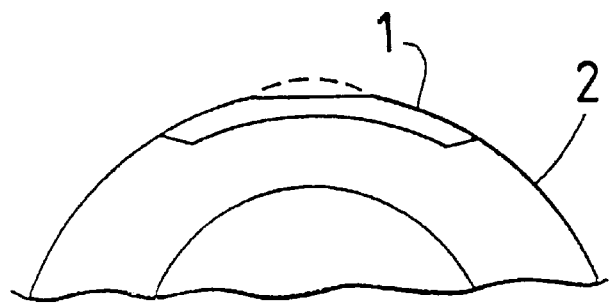
FIG. 3 is a schematic illustration showing the cornea after myopia correction.
Figure 4:
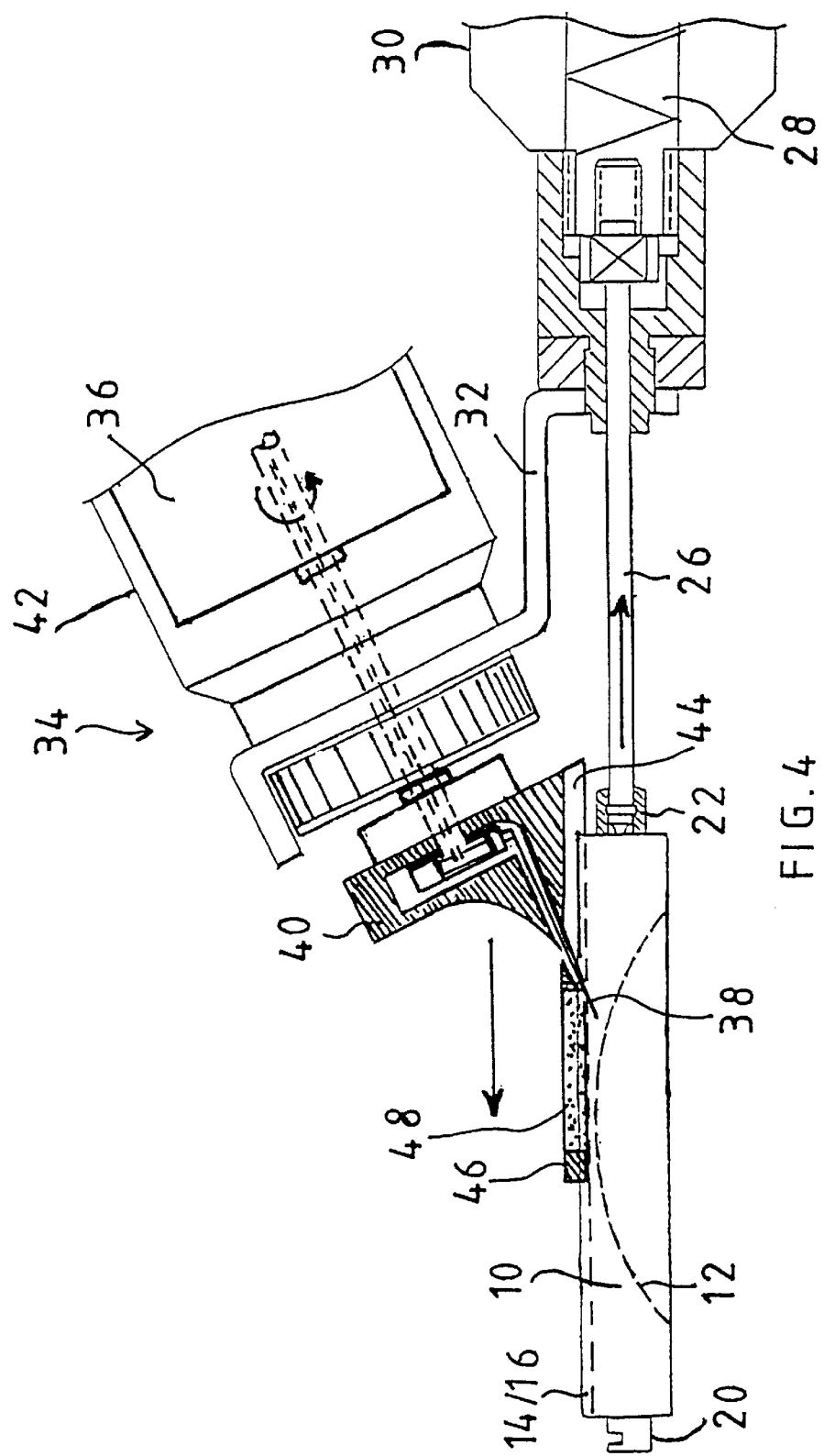
FIG. 4 is an elevation view partly in section illustrating a first form of the apparatus for performing the transverse cutting of the cornea according to the present invention.
Figure 5:
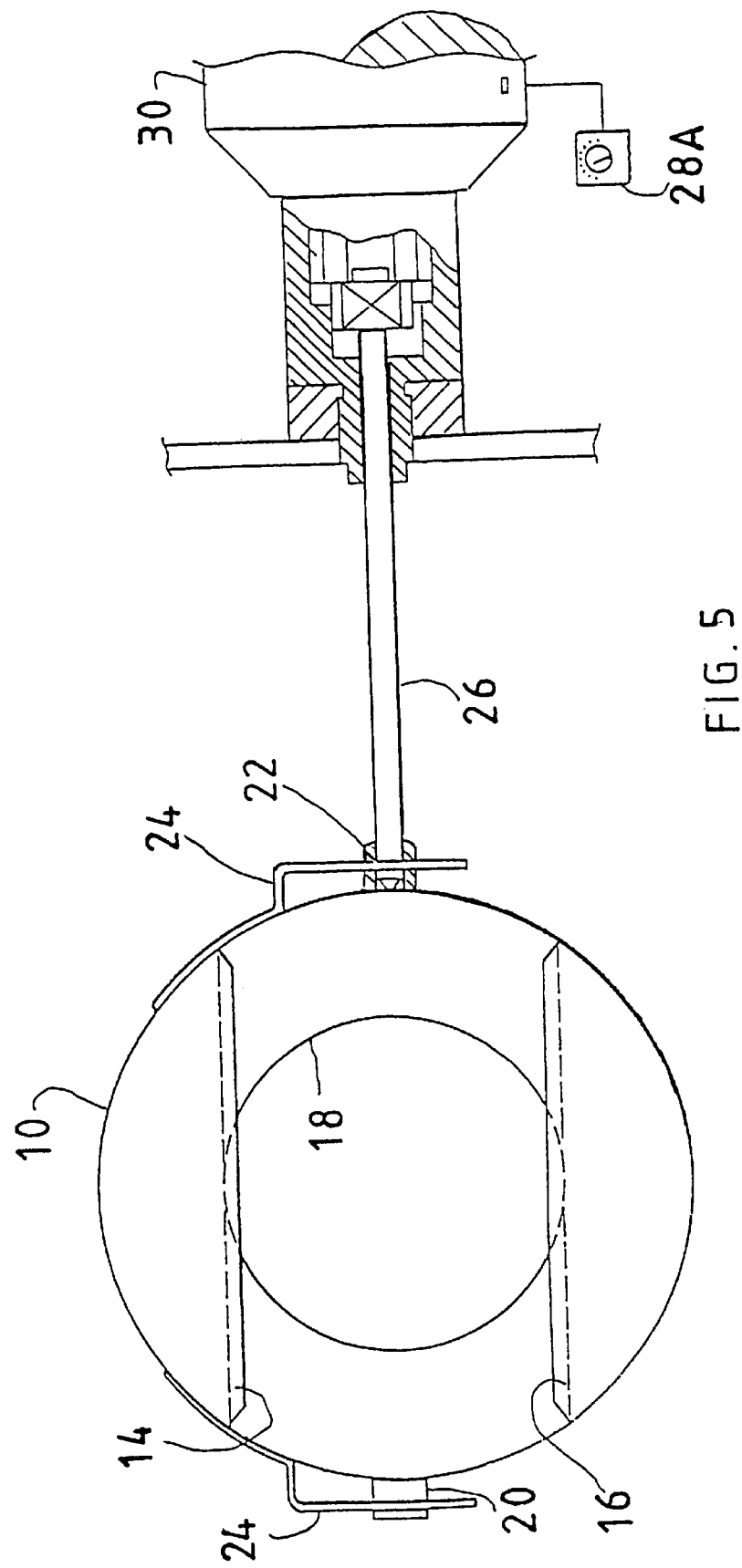
FIG. 5 is a partial plan view or the suction ring and a part of the actuator.

For the purposes of disclosing of a first embodiment of the present invention as shown in FIGS. 4 and 5 there is illustrated a cornea suction ring 10 having annular side walls and a concave bottom wall 12 having a shape for affixing to the cornea of the eye by suction in a manner as per se well known in the art. On the top surface of the cornea suction ring 10 which is opposite the corneal engaging surface there are formed dove tail guide surfaces 14 and 16 that are spaced apparat in parallel extending along opposite sides of an aperture 18 in the suction ring 10. Affixed to the outer peripheral surface of the suction ring at diametrically opposite sites are receiver sockets 20 and 22. The receiver sockets 20 and 22 are centrally spaced between the parallel arrangement of dove tail guide surfaces 14 and 16. Associated with each of the receiver sockets 20 and 22 is a spring clamp 24 which is urged under a resilient force of this spring into a slot traversing the sockets so that a part of clamp 24 protrudes into a receiving cavity of each receiver socket 20 and 22 to engage in an annular recess formed on the end portion of a shifting member 26. The shifting member 26 is connected to a linearly moveable output member of an electronically geared stepping motor 28 that is operated by a controller 28A so that the linear output speed is controllably selected at a given speed usually within the range of 0.5 mm/second to 3 mm/second. Fastened to the housing 30 of stepping motor 28 is an angled bracket 32 which forms a mounting structure for mechanically connecting a microkeratome 34.

The microkeratome 34 is per se well known in the art and includes a motor 36 for oscillating movement of a cutting blade 38 guided in a cutting head 40. This cutting head 40 is detachably mounted to a housing 42 of the motor 36 and is provided with guide surfaces 44 insertable for mating engagement into the guide surfaces 14 and 16 of the suction ring 10.

In front of the cutting edge of the cutting blade 38 the cutting head 40 comprises and applanation plate 46 having a transparent window 48 through which the field of operator is visible during operation. The stepping motor 28 of the actuator 28, 30 operates to move the microkeratome 34 relative to the cornea suction ring similar like a carpenter's plain. Forces producing this movement are exerted centrally by the positioning of the shift member 26 with respect to the parallel arrangement of the guide surfaces 14, 16 and 44 and this arrangement assures movement of microkeratome 34 without the risk of binding. The movements are related to each other so that the suction ring 10 may move towards or away from the housing 30 of the stepping motor 28, or if the suction ring is held, then the housing 30 of the stepping motor 28 will move towards and away from the suction ring 10. Thereby also moving the microkeratome 34 along the guide surfaces 14 and 16 (see the arrows in FIG. 4).

The control of the stepping motor 28, in addition to speed, controls the total movement of the microkeratome 34 through establishment of the distance that the shifting member 26 is moved relative to the housing 30 of the stepping motor 28 in this manner, the cut of the corneal tissue by the microkeratome 34 establishes the widths of the hinge attaching the lamella flap to the cornea.

Figure 6:
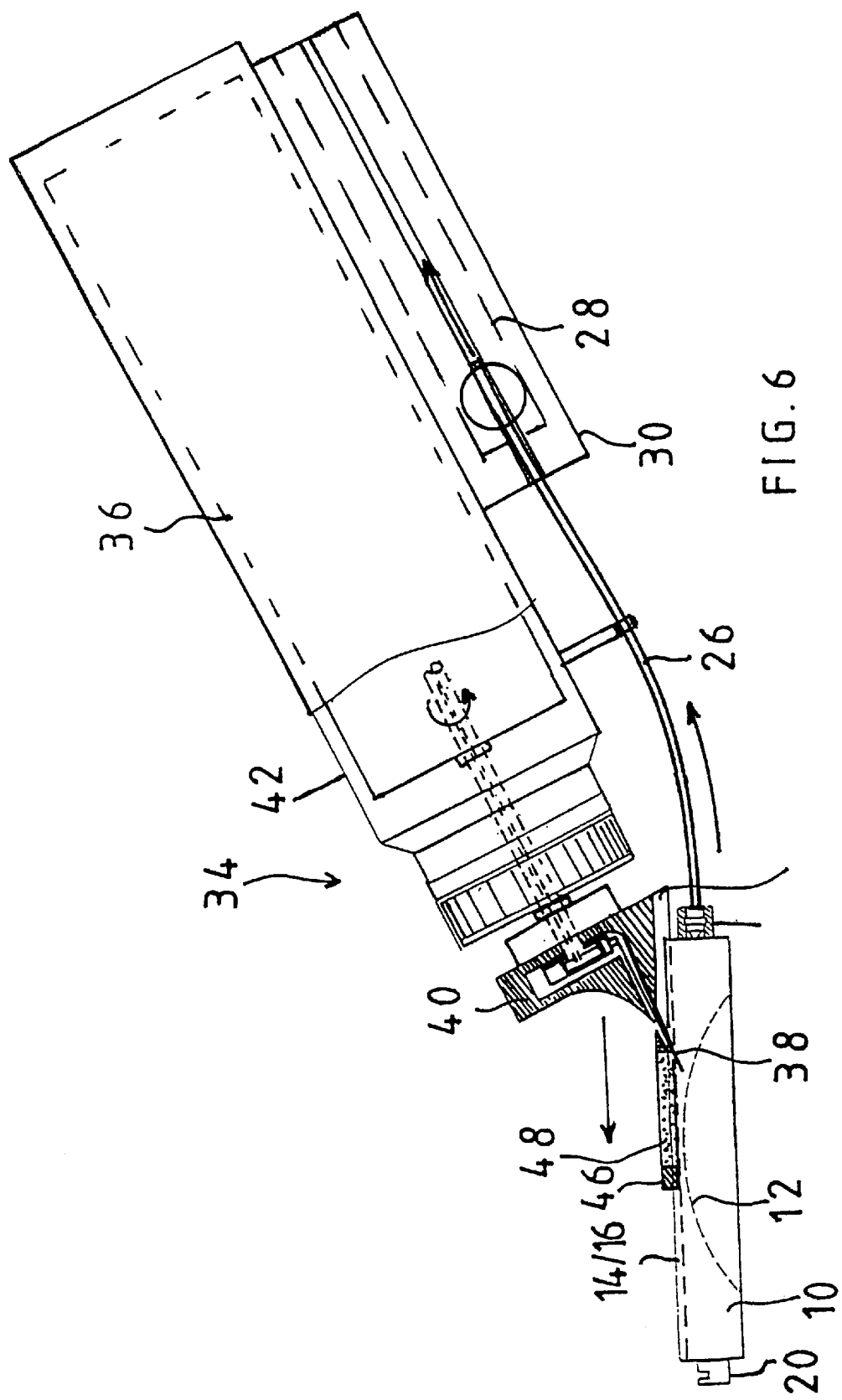
FIG. 6 is an elevation view partly in section illustrating a second form of the apparatus for performing the transverse cutting of the cornea according to the present invention.

The second embodiment of the invention illustrated in FIG. 6 replaces the stiff shift member 26 by a flexible, flat steel band. Accordingly, the motor housing 30 of the stepping motor 28 can be connected to or combined with the motor housing 42 of the oscillating motor 36 of the microkeratome 34 in a parallel arrangement as illustrated in FIG. 6.

While the present invention has been described in connection only with the preferred embodiments, it is to understood that other similar embodiments may be used or modifications or additions may be made to the described embodiments for performing the same function of the present invention without deveating therefrom. Therefore the present invention should not be limited to a single embodiment, but rather construed in breadth and scope in accordance with the recitation of the appended claims.

I claim:

1. An apparatus for transverse planar cutting of a cornea to expose a corneal surface to allow correction of myopia, said apparatus including:

a corneal suction ring comprising a cornea engaging surface on one side thereof and microkeratome guide surfaces at the opposite side thereof extending parallel along opposite sides of an aperture in said suction ring for exposing a portion of the cornea;

a microkeratome to execute at least a partial transverse cut of cornea surface when moving across said aperture of said suction ring;

said microkeratome comprising a cutting head, a motor housing and a motor for oscillating movement of a cutting blade guided in said cutting head;

whereby said cutting head is provided with guide surfaces insertable for mating engagement into the guide surfaces of said suction ring;

and an electronically controllable actuator for controlling relative movement between said suction ring and said cutting head comprising an actuator housing and a stepping motor within this housing to drive a shift member which is linear displaceable relatively to this housing;

whereby the actuator housing is rigidly connected to or combined with the motor housing of said microkeratome and said shift member is releasably connected to said suction ring.

2. The apparatus according to claim 1 wherein said shift member extends radially from said suction ring and in a generally parallel and central relation to the guide faces of the suction ring.

3. The apparatus according to claim 2 wherein the suction ring includes a receiver having a cavity for receiving an end portion of said shift member and a retainer supported by the suction ring to maintain a releasable interconnected relation between the shift member and the suction ring.

4. The apparatus according to claim 3 wherein said end portion said shift member is insertable into said receiving cavity in the direction of its displacement.

5. The apparatus according to claim 1 wherein the mating guide surfaces of the suction ring and of the cutting head have dove tail form.

6. The apparatus according to any of claim 1 to 5 wherein said shift member is a flat, flexible steel band.

7. The apparatus according to claim 1 wherein said cutting head is detachably mounted to said motor housing.

8. The apparatus according to claim 1 wherein said cutting head comprises an applanation plate having a transparent window in front of the cutting edge of said cutting blade.

* * * * *